United States Patent [19]

Suehiro et al.

[11] Patent Number: 4,925,803

[45] Date of Patent: May 15, 1990

[54] FIBROUS ROLL OF TUBULAR BRAID FOR IMMOBILIZATION OF CELLS AND ENZYMES

[75] Inventors: Tetsuro Suehiro, Tokyo; Aizo Yamauchi, Ibaraki; Hisao Ichijo, Ibaraki; Jun'ichi Nagasawa, Ibaraki; Noboru Aisaka, Ibaraki, all of Japan

[73] Assignee: Agency of Industrial Science & Technology, Ministry of International Trade & Industry, Tokyo, Japan

[21] Appl. No.: 107,051

[22] Filed: Oct. 13, 1987

[30] Foreign Application Priority Data

Oct. 13, 1986 [JP] Japan ................... 61-242267

[51] Int. Cl.$^5$ ............... C12M 1/40; C12N 11/00; C12N 11/02; C12N 11/08
[52] U.S. Cl. .................................. 435/288; 435/174; 435/177; 435/180; 435/182; 435/240.23
[58] Field of Search ............... 435/174, 177, 180, 182, 435/240.33, 288

[56] References Cited

U.S. PATENT DOCUMENTS 4,307,151  12/1981  Yamauchi et al. ............ 435/180 X

FOREIGN PATENT DOCUMENTS 0122039  7/1983  Japan ................... 435/180

OTHER PUBLICATIONS

Olson et al., Immobilized Enzymes in Food and Microbial Processes, Plenum Press, N.Y., 1974, pp. 176–179.
Marconi et al., Enzyme Engineering, vol. 3, 1980, pp. 269–278.

Primary Examiner—David M. Naff
Attorney, Agent, or Firm—Oblon, Spivak, McClelland, Maier & Neustadt

[57] ABSTRACT

A fibrous support for immobilizing enzymes and cells is prepared as a roll formed by winding a braid on a tubular frame member. The braid is formed in a tubular shape with a plurality of rovings containing very thin long filaments. The roll is formed by cross-winding of the braid to crush intersecting portions of the tubular braid flat. The roll of braid has an external void ratio of 15 to 30%. The thin long filaments of the tubular braid are obtained by spinning a mixture of polymers to form a plurality of fibers containing a soluble component and an insoluble component, joining the fibers to form a roving, forming a tubular braid from a plurality of the rovings and washing the braid to dissolve out the soluble component to produce separated thin long filaments of the insoluble component.

11 Claims, 3 Drawing Sheets

FIBROUS ROLL OF TUBULAR BRAID FOR IMMOBILIZATION OF CELLS AND ENZYMES

BACKGROUND OF THE INVENTION

1. Field of the Invention

This invention relates to a support, specifically a fibrous support adapted to support an enzyme, a microorganism, or cells thereon in an immobilized state and used as contained in a reaction vessel, for example, and to a method for the production of the fibrous support thereof.

2. Prior Art Statement

In recent years, immobilized enzymes, i.e. enzymes immobilized on suitable carriers, have been finding utility in the continuous production of various organic acids and saccharides. The advantage of this utility in terms of quality of product, cost of production, and economy of energy consumption has been attracting keen attention.

The methods available for the immobilization of enzymes are broadly grouped under the gel-entrapping method, the cross-linking method, and the carrier binding method. The carrier binding method can be further subgrouped into the covalent bond method, the ionic bond method, and the physical adsorption method. The immobilized enzymes obtained by these methods are generally in the form of gel, granules, or film and are used as packed in reaction vessels such as columns. These methods are applied not only to enzymes but equally to microorganisms and cells.

In uses of this type, the total capacity for treatment per unit volume of support and the speed of treatment, i.e. the volume of a gas or a liquid (hereinafter referred to as "fluid") to be treated per unit time, are matters of concern. For the purpose of improving the speed of treatment, the granular immobilized enzymes of reduced size are currently in common use. The effect of this size reduction consists in increasing the area of contact per unit volume of support and decreasing the distance of diffusion of materials in fluid within particles.

The size reduction of granule, however, increases the resistance the bed of the support offers to the fluid being passed therethrough. There is a possibility that in extreme cases, the passage of the fluid under treatment will become very difficult to achieve.

The method for immobilizing enzymes on fibers has also been proposed in the art (Japanese Patent Publication Nos. Sho 55(1980)-47130, Sho 57(1982)-17083, and Sho 57(1982)-17087, etc.).

The support having an enzyme immobilized on fibers, as compared with the granular support, has an advantage that it permits secondary fabrication into yarns, cords, woven fabric, knitted fabric, non-woven fabric, felt, or mat and enjoys a high speed of treatment. The advantage is ascribable to the fact that the individual filaments which make up the support are slender columns and, therefore, have a large area of contact and a short distance of internal diffusion. And the fibrous support offers smaller resistance to a fluid compared to that of a granular support, because of the bulkiness characteristic of fibrous materials.

In connection with the fibrous support described above, the idea of efficiently attaining an enzymatic reaction by means of an enzyme effectively immobilized on fibers having an average diameter of less than 1 $\mu$m has been disclosed to the art.

The fibrous support, however, generally has a disadvantage that it is liable to undergo compaction when it is continuously used for treating a fluid in motion at a high flow rate. This compaction is caused by the resistance offered by the fluid in motion and, in consequence of this compaction, the support itself gains in its own resistance offered to the fluid and further accelerates the progress of the compaction, starting a vicious cycle of increasing resistance and accelerating compaction. Once the compaction occurs in the support, it progresses rapidly even to the point where the treatment of the fluid will become substantially impracticable.

This phenomenon of compaction is liable to occur where the fibers have low bending rigidity, namely the component filaments are made of a soft substance and have a small diameter. The aforementioned fibers having an enzyme immobilized thereon are very thin and liable to be softened and, therefore, exhibit extremely low bending rigidity under water. When these fibers are used as a support without any modification, they are liable to undergo very serious compaction.

OBJECT AND SUMMARY OF THE INVENTION

An object of this invention is to provide a fibrous support of a novel construction capable of treating a fluid stably at a high speed continuously for a long time without inducing the phenomenon of compaction.

To accomplish the object described above according to the present invention, there is provided a fibrous support, comprising a tubular frame member and a roll formed by winding up a braid on the frame member as a core, the braid is formed in a tubular shape with a plurality of very thin long filaments and the roll is formed by cross-winding of the braid with tension enough to crush intersecting portions of the tubular braid flat and voids are formed between neighboring winds of the braid.

The roll, after having an enzyme immobilized thereon, is set in place within a reaction vessel. When a fluid under treatment is brought into contact with the roll, it flows through the voids between neighboring winds of the braid and the braid in the roll will not yield to compaction even after a protracted use. Since the intersecting portions of the braid in the roll become flat and are held fast to each other, the roll of the braid will not collapse and can be stably utilized for the reaction for a long time.

The above and other objects and features of the invention will become more apparent from the following detailed description with reference to the accompanying drawings.

DETAILED DESCRIPTION OF THE PREFERRED EMBODIMENT

Figure 1:
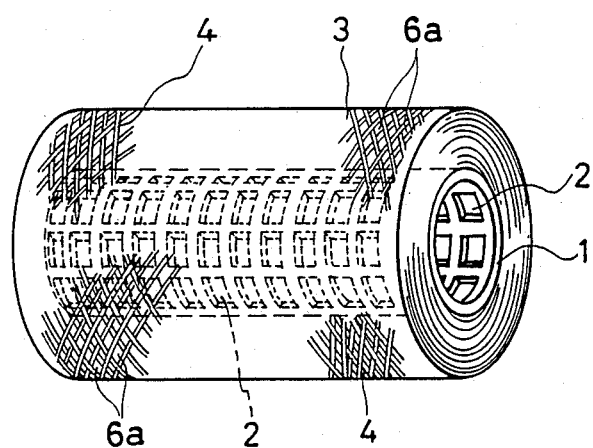
FIG. 1 is a perspective view showing a fibrous support according to the present invention.

The very thin long filaments to be used in the present invention will be described first. These filaments are produced by mixing two or more polymers different in kind, spinning the resultant mixture, and solving and removing soluble components from the spun fibers thereby allowing the produced fibers to acquire a very small diameter. Particularly, fibers of the polyvinyl alcohol type can be used advantageously.

To be specific, a partially saponified polyvinyl alcohol having an average polymerization degree of 800 to 1,700 and a saponification degree of 85 to 90 mol % and a highly saponified polyvinyl alcohol are mixed in a ratio in the range of 5:5 to 7:3 to prepare a spinning dope. By dry spinning this spinning dope, fiber bundles are obtained which are formed of insoluble fibrils formed of a polymer containing the completely saponified polyvinyl alcohol. The average diameter of the fibers obtained as described above generally falls in the range of 10 to 30 μm and the number of insoluble fibrils contained in each of the fibers is approximately in the range of 2,000 to 20,000.

Then, a prescribed number of fiber bundles emanating from as many spinning nozzles in the spinning step are joined to form rovings. In this case, the number of fiber bundles forming each roving is in the range of approximately 3 to 10.

As described above, this invention uses rovings formed by fiber bundles obtained by the mixed spinning. Owing to this special treatment, the fibrous support eventually produced is allowed to acquire a sufficient area of contact with the fluid, obtain ample activity stably, exhibit sufficient strength after the braiding step, and endure very high winding tension even after the fibers have been finely divided. The fiber dividing step and the winding step will be described more fully later. Finally the roving is cross-wound to form a roll which functions as the support, which is capable of resisting compaction due to the pressure of the fluid under treatment for a very long time.

Then, a braid is formed with the rovings. The term "braid", as known, means a cord obtained by causing three or more component strands to be plaited in a regular crisscross pattern. In the present invention, a tubular braid containing a hollow space is formed with 8 to 20 joined rovings. Though the average diameter of the braid should be selected to suit the purpose for which the produced support is used, it is desired to fall in the range of 0.5 to 2.0 mm.

If the plurality of fibers are simply twisted together to form a twisted cord instead of a braid, since the twist imparted to the twisted cord is loosened to a great extent during the subsequent step of division of fibers into thin filaments, the twisted cord will no longer retain enough strength to withstand the impact exerted thereon during the subsequent winding step. Moreover, by its very nature, the twisted cord cannot be produced in the form of a hollow tube like that of the braid.

Then, the braid is washed with water to effect conversion of the joined fibers composing the rovings into thin filaments. This treatment of washing with water may, for example, be effected by immersing the braid in water at room temperature and a washing-out treatment. In consequence of the treatment, the soluble fibrils of the partially saponified polyvinyl alcohol are dissolved out of the fibers and the individual fibers are each separated into a plurality of very thin long filaments of insoluble fibrils. The diameters of the very thin long filaments fall in the range of 0.1 to 1.0 μm.

If the average diameter of these very thin filaments exceeds 1 μm, the surface area of the filaments and the amount of the enzyme immobilized on the filaments are so small as to lower the activity of the produced fibrous support. If the average diameter is less than 0.1 μm, the filaments are liable to make the spinning and subsequent processing thereof difficult.

If the conversion of each fiber into very thin filaments is carried out when the filaments are in the form of fiber bundles or rovings formed of such fiber bundles, they undergo much degradation of strength similarly to the twisted cord and fail to endure the subsequent braiding step. Specifically, the very thin filaments are readily broken by friction.

When the conversion of joined fibers into very thin filaments is carried out when the fibers are in the form of a braid, the braid is allowed to retain its construction, though it the texture thereof becomes proportionately loosened. Thus, the braid retains enough strength to endure the subsequent winding step. This partial loosening of the braid proves rather advantageous in the sense of facilitating solid-liquid contact and contributes to enhancement of the efficiency of activity.

The very thin long filaments of the braid are then subjected to a treatment of aminoacetalization for the purpose of improving the ratio of immobilization of an enzyme.

This aminoacetalization requires use of an aldehyde. As examples of the aldehyde, there can be cited aminoacetaldehyde, monomethyl aminoacetaldehyde, dimethyl aminoacetaldehyde, trimethyl monoformyl ethyl ammonium halides, monoethyl aminoacetaldehyde, diethyl aminoacetaldehyde, triethyl monoformyl ethyl ammonium halides, 3-amino propion aldehyde, 3-monomethyl aminopropion aldehyde, aminobenzaldehyde, monomethyl aminobenzaldehyde, dimethyl aminobenzaldehyde, and acetals thereof.

The reaction of the polyvinyl alcohol or polyvinyl alcohol type synthetic with the aminoacetalizing agent can be carried out advantageously by using a mineral acid such as sulfuric acid or hydrochloric acid as a catalyst and optionally using Glauber's salt or table salt as an impregnation inhibitor.

The swelling ratio of the very thin filaments of aminoacetalized polyvinyl alcohol has a conspicuous effect upon the adsorptive activity of the immobilized enzyme and the enzymatic activity itself. For the purpose of this invention, the swelling ratio is desired to be suitably adjusted in due consideration of the kind of the enzyme and the conditions of use of the enzyme. Desirably, this swelling ratio is in the range of 1.5 to 5.0 as the equilibrium ratio under water at 30° C. This adjustment can be obtained by suitably selecting the ratio of extension of filaments and the temperature of heat treatment and optionally using acetalization with formaldehyde or glutanaldehyde.

Then, the tubular braid formed of the very thin long filaments is wound up on the frame member 1 as a core to produce the roll (fibrous support) 3 as shown in FIG. 1.

The frame member 1 has the shape of a tube and possesses a plurality of through holes 2 in the wall of the tube. The material, dimensions, and shape of the frame member and the shape, size, number, and distribution of the through holes may be suitably fixed to suit the purpose for which the frame member is used. Generally, the frame member has a diameter in the range of 20 to 40 mm and a length in the range of 100 to 300 mm.

The roll 3 to be formed by winding up the tubular braid 4 on the frame member 1 may be produced in any conventional shape such as cheese or cone which has winding angles produced by a traverse cam. For the uniformization of the flow of the fluid under treatment, the roll is desired to be in the shape of a straight cheese.

In the roll 3, two kind of voids are formed. One is formed between neighboring winds of the braid 4 by aforementioned cross-winding with traverse motion (External Void 6a). The other is the hollow portion of the tubular braid (Internal Void 6b). The external void 6a functions as a flow channel for fluid under treatment. And the volume fraction of this external void in the roll (External Void Ratio) is desired to fall in the range of 15 to 30%. If the external void ratio exceeds 30%, the capacity for activity is not sufficient. If the void ratio is than 15% the loss is unduly large.

In the present invention, the braid is wound up on the frame member, with the traverse controlled so as to produce proper external voids in the finished roll.

The winding of the braid is carried out in such a way as to preclude the phenomenon of ribboning or cobwebbing, ensure formation of a uniform roll enough to prevent uneven flow of the fluid therethrough and, at the same time, and prevent the occurrence of loose traverse or bulge on the opposite end portions of a roll by way of preventing leakage of the fluid through the opposite end portions of the roll when the roll is set in the reaction vessel and used. For safe winding, it suffices to follow the conventional method faithfully.

Figure 2:
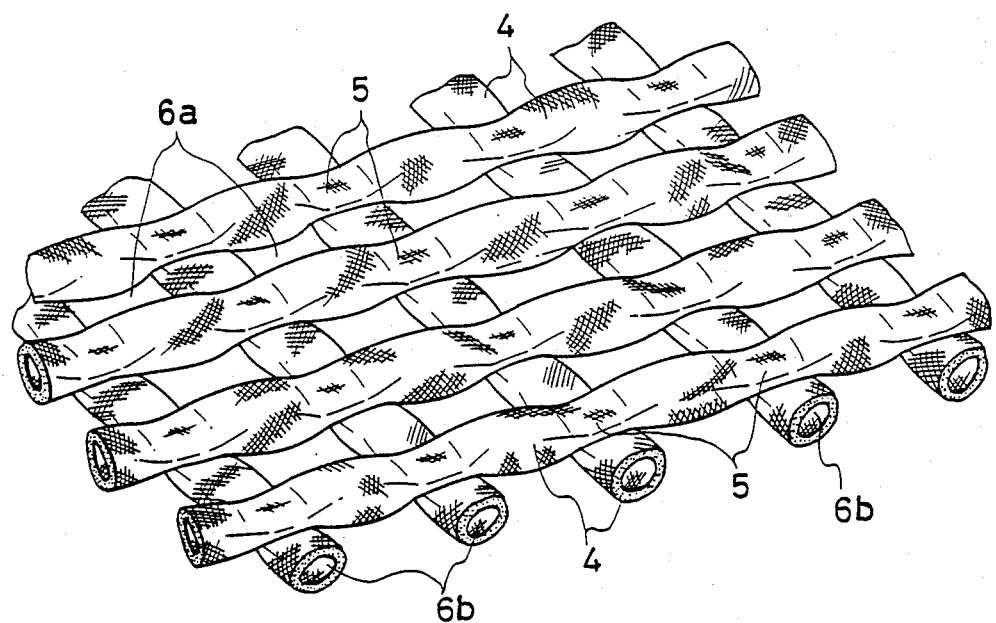
FIG. 2 is an enlarged perspective view showing the intersecting portions of braids constituting a fibrous support of FIG. 1.
Figure 3:
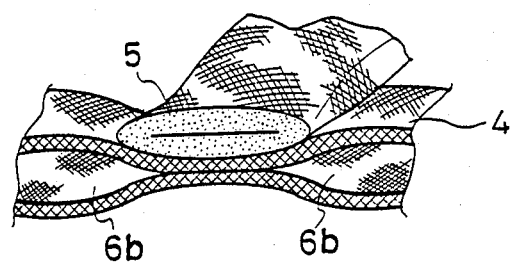
FIG. 3 is a cross-sectional view showing the intersecting portion of the braid of FIG. 2.

Particularly the desire to wind up the braid 4 so as to ensure inclusion of required external voids 6a in the roll 3 and, at the same time, preclude possible deformation of the finished roll is met by a method which comprises tightly squeezing the all intersecting portions 5 of superposed plies of the braid 4 enough to crush the corresponding portions of the internal voids of the braid flat as shown in FIGS. 2 and 3. The other portions of the braid, which do not intersect, are allowed to retain the voids 6b, though loosely and enable the materials under treatment to diffuse quickly through the braid of the roll. The roll, therefore, is prevented from compaction or deformation due to the pressure of the flow of the fluid under treatment.

One of the winding conditions resides in keeping the winding angle slightly large, in the range of 15° to 22°. To meet this condition in the case of a roll having a diameter of 65 mm and a traverse length of 125 mm, for example, the winding operation is regulated so that the number of winds will fall in the range of 1.46 to 2.28 and the pitch of the braids, as observed in every layer of the winding, will fall in the range of one and a half to twice of the thickness of the braid. Moreover, the braids in adjacent layers of the winding are offset from each other by 0.5 to 1.0 the thickness of the braid.

After the braid has been wound up in a roll on the frame member as described above, a given enzyme is immobilized on the very thin long filaments of the braid.

As examples of the enzyme suitable for the immobilization, there may be cited glucose isomerase, invertase, urease, glucoamylase, glucoxidase, ribonuclease, and protease. Any enzyme other than those cited above can also be used for immobilization.

The immobilization of the enzyme can be carried out by any of the conventional methods such as a method which comprises immersing the roll of braid in a solution of the enzyme and stirring the roll therein or a method which comprises setting the roll wound up on the frame member in place inside a reaction vessel destined to be used for the reaction aimed at and passing a solution of the enzyme through the reaction vessel. The immobilization of enzyme mentioned above is effected by virtue of the adsorption due to the Coulomb attraction. The object of this immobilization is not limited to enzymes but may embrace various microorganisms or cells.

The fibrous support fabricated as described above is set in place in a reaction vessel in the form of a column of a cartridge and put to use.

Figure 4:
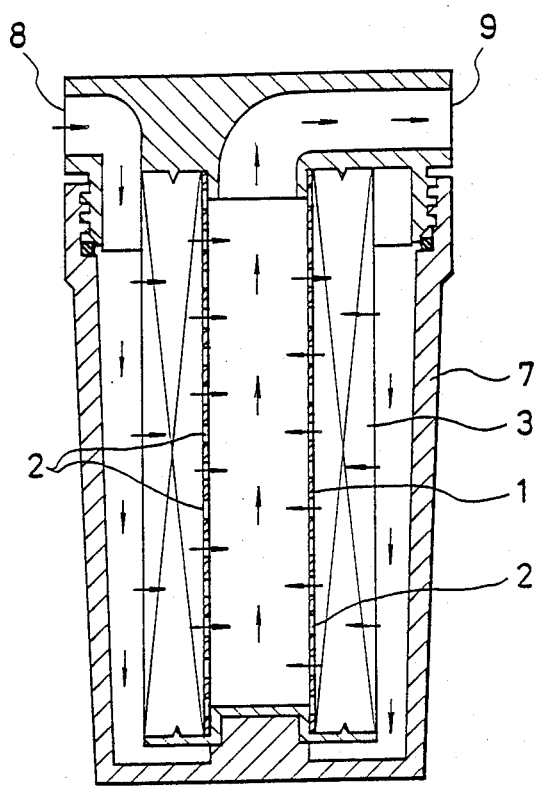
FIG. 4 is a cross-sectional view illustrating a fibrous support of the present invention in a state set in place in a reaction vessel.

FIG. 4 depicts a typical configuration having the fibrous support (roll 3) of the present invention set in place in a reaction vessel 7. A fluid subjected to treatment is introduced in a pressed state through an inlet 8, allowed to flow through the external voids between the braid on the roll 3 wound on a tubular frame member 1 and continue the flow through holes 2 in the frame member 1, and led into the interior of the frame member 1. During this passage, the fluid comes into contact with and reacts with the enzyme immobilized on the very thin long filaments of the roll 3. The fluid which has undergone this reaction is withdrawn through an outlet 9.

The combination of an enzyme and a fluid for treatment can be widely varied to suit the purpose of the operation.

In accordance with the present invention, even when the enzyme is immobilized on a fibrous support using very thin filaments having an average diameter of not more than 1 $\mu$m, the produced fibrous support can stably treat the fluid for a long time.

The reason for this stable treatment attained by the fibrous support is that the braid originally formed in a hollow construction, while being wound up on the frame member, is tightly squeezed to permit the every intersecting portions of the braid to be crushed flat and, as a result, the produced roll acquires a stable shape such that the braid of the roll will neither come loose nor entangle even when the fluid under treatment exerts high pressure upon the fibrous support and the fluid, consequently, is allowed to flow safely through the voids between neighboring winds of the braid.

The idea of allowing the enzyme-immobilized fibers to be exposed to the fluid under treatment in a state wound up on a core as contemplated by the present invention may appear to resemble a method of treating whey with lactase enzyme immobilized on a fiber roll. (Enzyme Engineering, Vol 5, pp 269, Plenum Publishing Corporation, 1980).

They are two clearly different methods, however, because the cheese whey treatment method is directed to treating a spun yarn wound up in a roll, whereas the method of the present invention is directed to treating a fluid passing through a roll of braid.

The braid in the roll used in the fibrous support of this invention, therefore, tolerates occurrence therein of portions with which the fluid under treatment fails to come into contact.

Specifically, the opposite end portions of the roll of the present invention inevitably have a higher winding density and permit substantially no flow of the fluid. When the fibrous support is set in place and put to use, these terminal portions function as seal portions and prevent the fluid under treatment from passing through the roll without coming into contact with the activated portion of the roll. In the present invention, since the braid is tightly wound up in a roll for the purpose of preventing compaction and ensuring safe contact during the protracted service of the fibrous support as described above, the sealing effect of the opposite end portions of the roll is particularly conspicuous. In cheese whey treating method, this effect would inevitably result in uneven treatment. Conversely, the cheese whey treating method tolerates part of the whey solution passing through the roll without coming into contact with the thread of the roll. Thus, the requirement of the cheese whey treating method is entirely different from that of the present invention.

The cheese whey treating method and the present invention are based on entirely different technical ideas.

Now, the present invention will be described more specifically below with reference to examples. It should be noted, however, that this invention is not limited to these examples.

EXAMPLE 1

With a static mixer (20 elements) disposed immediately in front of a spinning nozzle, an aqueous solution having perfectly saponified polyvinyl alcohol of an average polymerization degree of 1,200 dissolved therein by heating in a concentration of 34% by weight and an aqueous solution of 30% by weight of polyethylene oxide of an average molecular weight of 750,000 were mixed in a gravimetric polyvinyl alcohol/polyethylene oxide ratio of 48/52. The mixture was immediately dry spun through a nozzle with 60 orifices. The spun threads of the mixture were stretched to 4.5 times the original length and heat treated at 235° C., to produce a bundle of heat-treated fibers of the mixture of polyvinyl alcohol/polyethylene oxide 250 deniers in thickness.

Then a roving of 1,000 deniers was produced by joining four such fibers. From 16 such rovings, a tubular braid 1.6 mm in diameter was obtained.

This braid was washed with water to dissolve and remove the polyethylene oxide component and effect separation of the individual filaments each into about 2,500 very fine polyvinyl alcohol fibers having an average diameter of 0.2 μm. Subsequently, in a reaction bath composed of 5% of HCl, 15% of NaCl, 0.3% of dimethyl aminoacetaldehyde, and 79.7% of water by weight, the braid of finely separated fibers was left standing at a bath ratio of 1:20 at 60° C. for eight hours, to effect conversion of the fibers into very thin aminoacetalized polyvinyl alcohol filaments having an aminoacetalization degree of 2.8 mol %. These filaments were found to possess a softening point of 65° C. in water and a swelling ratio of 3.2 in water at 30° C.

The braid consequently obtained was wound up on a frame member as a core. The roll was produced in the shape of a straight cheese. The physical constants of this roll were as shown below.

TABLE 1

| | |
|---|---|
| Total void | (about) 73% |
| External void | 28% |
| Internal void | 60% |
| Length of braid wound | 128 m |
| Weight of braid | 102.4 g |
| Length of traverse | 120 mm |
| Number of winds | 1.94 |

TABLE 1-continued

| | |
|---|---|
| Winding angle on surface | 17.6° |

The voids were determined as follows.

First, the roll was submerged in water to measure buoyancy and find the true volume of the fibrous support by subtracting the known volume of the frame member. Then, the water within the external voids as a flow channel formed between neighboring winds of the braid was removed by centrifugation and the roll was weighed. The roll was further dried and again weighed. From the difference between the two weights, the weight of water retained within the braid, namely the internal voids could be determined. The external voids could be obtained by subtracting the volume of the internal voids and the true volume of the fibrous support from the volume of the support calculated from the visible dimensions thereof.

The roll (fibrous support) was set in place within the reaction vessel constructed as shown in FIG. 4, and then, 1,500 ml of an aqueous invertase solution (activity unit 400 u/g) was circulated through the reaction vessel at 30° C. for five hours for immobilization of the invertase. The filaments of the roll on which the invertase had been immobilized were thoroughly washed with water and tested for ratio of immobilization of invertase. The ratio was found to be nearby 100%.

When an aqueous solution of 17% by weight of sucrose kept at 30° C. was circulated through the reaction vessel at a flow rate of 2 l/min, the enzymatic activity calculated from the initial speed of conversion of sucrose to glucose was as high as 101 u/g (ratio of manifestation 25.3%). The pressure difference for the aforementioned flow rate was 450 mm $H_2O$.

When this introduction of the aqueous sucrose solution was continued for two weeks, the residual activity of invertase was not less than 95% and the pressure difference was 500 mm $H_2O$.

For comparison, the aforementioned filament bundles were directly knitted on a roll calendar and subjected to the same conversion of individual filaments into very thin filaments, aminoacetalization, and enzymatic immobilization as in the preceding example. The knitted fabric was untied and the loose fibers were cut into short-staple fibers. The same amount of short fibers as the aforementioned fibrous support were packed in a column 75 mm in inside diameter and the aqueous solution was passed through the column. As the short fibers settled to form a packed bed, the flow of the solution became increasingly difficult. Finally, the flow volume was only 10 ml/min at a pressure difference of 2 $kg/cm^2$.

Separately, the same weight of the braid as in the aforementioned fibrous support was wound up in multiple plies to produce a roll of the shape of a solenoid. The resultant support showed a packing ratio of 52% and permitted absolutely no flow of the solution even at a pressure difference of 4 $kg/cm^2$.

A fibrous support was obtained by following the procedure of the example cited above, except that the physical constants shown in Table 2 below were used instead. circulated through the reaction vessel for two hours. It was found from the difference in concentration of yeast between the solutions before and after the circulation that the wet yeast immobilized on the roll weighed 13.2 g.

The roll within the reaction vessel was washed with water to remove the wet yeast which has not been immobilized on the roll.

After washing out unimmobilized enzyme from the reaction vessel with water, then a solution obtained by dissolving 1,250 g of honey in 5.6 l of water was circulated through the reaction vessel at a flow rate of 2 l/min to effect batchwise alcohol fermentation at 22.5° C. for five days. The concentrations of sugar and ethanol in the solution flowing through the reaction vessel, which varied as the time lapsed, were as shown below.

TABLE 4

| Time (Day) | Concentration (w/v %) | |
| --- | --- | --- |
| | Sugar | Ethanol |
| Initial | 15.9 | — |
| 1 | 12.5 | 1.2 |
| 2 | 8.4 | 3.1 |
| 3 | 5.5 | 4.9 |
| 4 | 2.8 | 6.0 |
| 5 | 1.6 | 6.6 |

A solution containing 200 g/l of honey was continuously passed through the reaction vessel at a flow rate of 40 ml/h for five days. The average value of the concentration of ethanol in the solution during the reaction process was about 92% of the last concentration of ethanol of the aforementioned batchwise alcohol fermentation.

After completion of the fermentation the reaction vessel was washed with water to thoroughly remove the fermentation solution and then the roll was taken out of the reaction vessel, dried and weighed. It was found that the weight of the dried roll increased was 68.4 g which corresponds to about 205.2 g of wet yeast. Therefore, it was found from the difference between this wet yeast and the initial wet yeast that about 192 g of wet yeast was increased in the state of being immobilized on the roll.

What is claimed is:

1. A fibrous support prepared by:
   providing a frame member having a tubular shape and having a plurality of through holes in the wall thereof;
   forming a tubular braid from a plurality of rovings which in turn are prepared from thin long filaments having diameters in the range of 0.1 to 1.0 μm; and
   cross-winding said tubular braid on said frame member and tightly squeezing all contacting, intersecting portions of the braid which flatly crushes these portions of the braid, thereby forming a roll of braid on said frame member with an external void ratio of the tubular braid in the roll ranging from 15 to 30%.

2. The fibrous support according to claim 1, wherein said thin filaments have an enzyme or cells immobilized thereon.

3. The fibrous support according to claim 1, wherein the roll of said braid formed on said frame member is in the shape of a straight cheese.

4. The fibrous support according to claim 1, wherein said thin long filaments are polyvinyl alcohol fibers.

5. The fibrous support according to claim 1, wherein said tubular braid has a diameter in the range of 0.5 to 2.0 mm.

6. The fibrous support according to claim 2, wherein said immobilized cells are cells of a microorganism.

7. A method for the production of a fibrous support, which comprises:
   mix spinning at least two polymers different in kind thereby forming a plurality of fibers containing a soluble component and an insoluble component,
   joining said plurality of fibers to form a roving,
   forming a tubular braid of a plurality of rovings,
   washing said braid to dissolve out said soluble component thereby producing separated very thin long filaments of the insoluble component, and
   cross-winding said tubular braid formed of said very thin long filaments around a frame member having the shape of a tube and having a plurality of through holes in the wall thereof and tightly squeezing all contacting, intersecting portions of said braid thereby flatly crushing these portions of the braid and forming a roll of braid on said frame member with an external void ratio of the tubular braid in the roll ranging from 15 to 30%.

8. The method according to claim 7, wherein the tubular braid wound onto the frame member has a pitch between one and a half and two times the thickness of the braid.

9. The method according to claim 7, wherein tubular braids in adjacent layers of the winding are offset from each other by between a half and one time the thickness of the braid.

10. The method according to claim 7, which further comprises a step of immobilizing an enzyme or cells on said very thin fibers of said braid forming said roll.

11. The method according to claim 10, wherein said immobilized cells are the cells of a microorganism.

* * * * *

UNITED STATES PATENT AND TRADEMARK OFFICE
CERTIFICATE OF CORRECTION

PATENT NO. : 4,925,803
DATED : MAY 15, 1990
INVENTOR(S) : SUEHIRO, ET AL

It is certified that error appears in the above-identified patent and that said Letters Patent is hereby corrected as shown below:

In claim 7, line 9, "thereby"

change to read, --from the fibers thereby--.

Signed and Sealed this

Twenty-ninth Day of June, 1993

Attest:

MICHAEL K. KIRK

Attesting Officer

Acting Commissioner of Patents and Trademarks